United States Patent [19]
Derieg et al.

[11] 3,965,151
[45] June 22, 1976

[54] INTERMEDIATES FOR TRICYCLIC BENZODIAZEPINES

[75] Inventors: Michael Edward Derieg, Caldwell; James Valentine Earley, Cedar Grove; Rodney Ian Fryer, North Caldwell; Leo Henryk Sternbach, Upper Montclair, all of N.J.

[73] Assignee: Hoffmann-La Roche Inc., Nutley, N.J.

[22] Filed: Mar. 11, 1975

[21] Appl. No.: 557,438

Related U.S. Application Data

[60] Division of Ser. No. 45,928, June 12, 1970, abandoned, which is a continuation-in-part of Ser. No. 26,068, April 6, 1970, Pat. No. 3,905,956, which is a continuation-in-part of Ser. No. 863,377, Oct. 2, 1969, abandoned, which is a continuation-in-part of Ser. No. 768,909, Oct. 18, 1968, abandoned.

[52] U.S. Cl. .................. 260/490; 260/239.3 T; 260/295 AM; 260/295 R; 260/463; 260/471 A; 260/562 B; 260/570 AB
[51] Int. Cl.² ............. C07C 97/10; C07C 103/42
[58] Field of Search .................................. 260/490

[56] References Cited
OTHER PUBLICATIONS
Chem. Abstracts, 69: 96796n.

Chem. Abstracts, 75: 76852y.

*Primary Examiner*—Vivian Garner
*Attorney, Agent, or Firm*—Samuel L. Welt; George M. Gould; Frank P. Hoffman

[57] ABSTRACT

Tricyclic benzodiazepine derivatives ("A") bearing a hydroxylower alkyl substituent in the 1-position and a heterocyclic ring joined between positions 4 and 5 of the benzodiazepine moiety are described. The heterocyclic ring will contain the nitrogen atom appearing at position 4 of the benzodiazepine ring as well as the hetero atom, which may be either oxygen or nitrogen, attached to the carbon atom at the 5-position of the benzodiazepine ring. "A" bearing an oxygen atom in the new heterocyclic ring may be formed from the corresponding 4,5-unsaturated benzodiazepines by treatment with an epoxide compound in the presence of an acid catalyst. "A" bearing either a nitrogen or an oxygen atom in the new heterocyclic ring may be prepared by cyclization of the corresponding open compound. "A" are useful as sedative, muscle relaxant and anti-convulsant agents.

4 Claims, No Drawings

INTERMEDIATES FOR TRICYCLIC BENZODIAZEPINES

CROSS REFERENCE TO RELATED APPLICATIONS

This is a division of application Ser. No. 45,928 filed June 12, 1970, now abandoned, which is a continuation-in-part of application Ser. No. 26,068 filed Apr. 6, 1970 now U.S. Pat. No. 3,905,956, which is a continuation-in-part of Ser. No. 863,377, filed Oct. 2, 1969, now abandoned, which in turn is a continuation-in-part of Ser. No. 768,909, filed Oct. 18, 1968, now abandoned.

DESCRIPTION OF THE INVENTION

The present invention relates to tricyclic benzodiazepines of the following formula

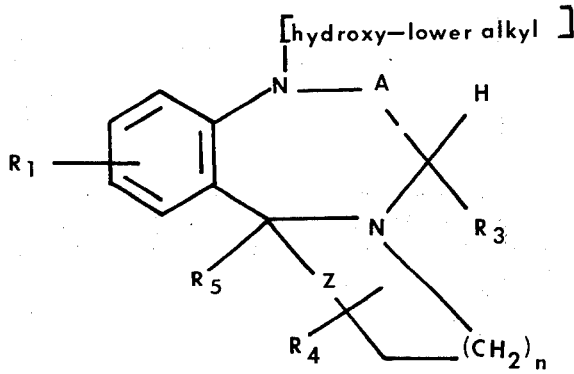

I wherein A is selected from the group consisting of —CH$_2$— and

Z is a hetero atom selected from the group consisting of —O— and

where R$_6$ is hydrogen, lower alkyl or acyl; n is an integer from 1 to 2; R$_1$ is hydrogen, halogen, nitro, trifluoromethyl, lower alkyl, lower alkyl mercapto or lower alkoxy; R$_3$ is hydrogen, lower alkyl or the group —COO-lower alkyl; R$_4$ is hydrogen, lower alkyl or —CH$_2$X where X is selected from the group consisting of chlorine, bromine, lower alkoxy, lower alkoxy-lower alkyl and di-lower alkylamino; and R$_5$ is pyridyl, phenyl and phenyl substituted with a member selected from the group consisting of halogen, nitro, trifluoromethyl, and lower alkyl.

As used herein, the term "lower alkyl," either alone or in combination as in lower alkoxy-lower alkyl, comprehends straight or branched chain hydrocarbon groups having from 1-7 carbon atoms, preferably 1-7 carbon atoms, such as methyl, ethyl, propyl, isopropyl and the like. The term "acyl" encompasses an organic radical derived by removal of a hydroxyl group from an organic acid, such as an alkanoic acid containing from 2-7 carbon atoms, for example propionyl and the like. The term "lower alkoxy" comprehends a lower alkyl group having an oxygen function substituted therein, such as methoxy, ethoxy, propoxy, etc. The term "halogen" represents all four forms thereof, i.e. fluorine, chlorine, bromine and iodine, unless expressly indicated otherwise. The term "lower alkanol" connotes primary, secondary, or tertiary saturated aliphatic alcohols such as methanol, ethanol, propanol, isopropanol and the like.

A preferred group of compounds falling within the scope of formula I are those wherein the hetero atom Z is oxygen, i.e. compounds of the formula

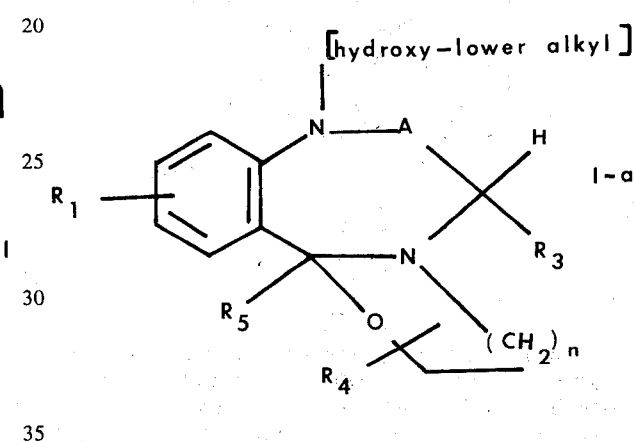

I-a wherein A, R$_1$, R$_3$-R$_5$, and n are as described above.

Another preferred embodiment of the present invention encompasses the compounds of formula I wherein the hetero atom Z is oxygen and wherein R$_1$ is selected from the group consisting of hydrogen, halogen, nitro, trifluoromethyl, or lower alkyl, i.e., compounds of the formula

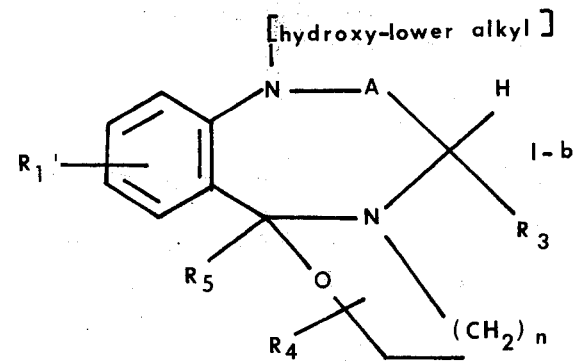

I-b wherein R$_1$' is selected from the group consisting of hydrogen, halogen, nitro, trifluoromethyl, and lower alkyl; A, n, and R$_3$-R$_5$ are as described above.

A further preferred embodiment of the present invention encompasses the compounds of formula I wherein the hetero atom Z is oxygen, $R_1$ is hydrogen or halogen, with chlorine being the preferred halogen, and is joined to the benzodiazepine moiety at the 7-position thereof; $R_3$ is hydrogen; $R_4$ is hydrogen, lower alkyl, most preferably methyl, or chloromethyl; and $R_5$ is phenyl or phenyl substituted at the ortho position with halogen, with fluorine being the most preferred halogen; i.e. compounds of the formula

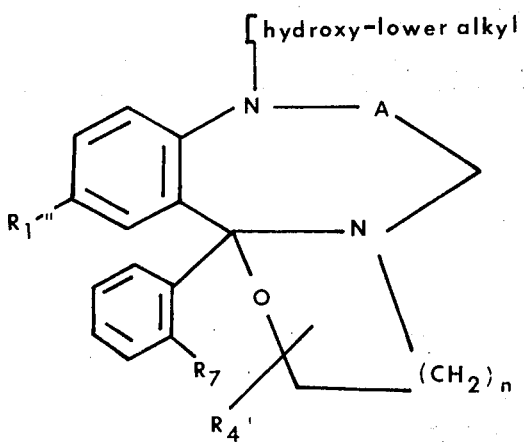

I-c wherein $R_1''$ is hydrogen or halogen; A and n are as described above; $R_4'$ is hydrogen, lower alkyl, or chloromethyl; and $R_7$ is hydrogen or halogen.

Most preferred among the compounds of formula I above are those wherein the hetero atom Z is oxygen; n is 1; $R_1$ is chlorine and is joined to the benzodiazepine moiety at the 7-position thereof; $R_3$ is hydrogen; $R_4$ is hydrogen, methyl or chloromethyl; and $R_5$ is phenyl or phenyl substituted in the ortho position with fluorine.

Another particular aspect of the present invention relates to compounds of formula I above wherein

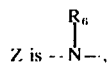

where $R_6$ is hydrogen, lower alkyl or acyl, i.e., compounds of the formula

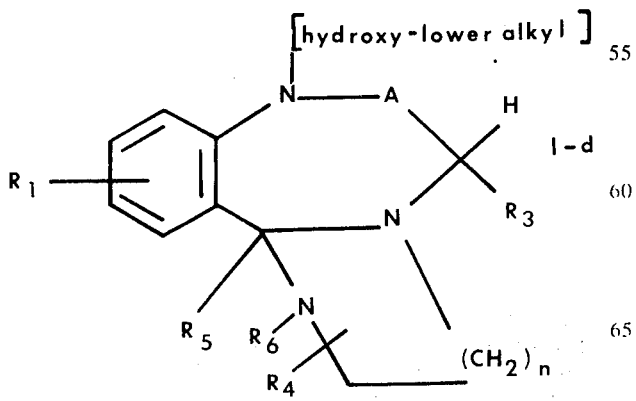

I-d wherein A, n, $R_1$, and $R_3$–$R_8$ are as described above.

Still another particular aspect of the present invention relates to compounds of formula I above wherein A represents the group —$CH_2$—, i.e., compounds of the formula

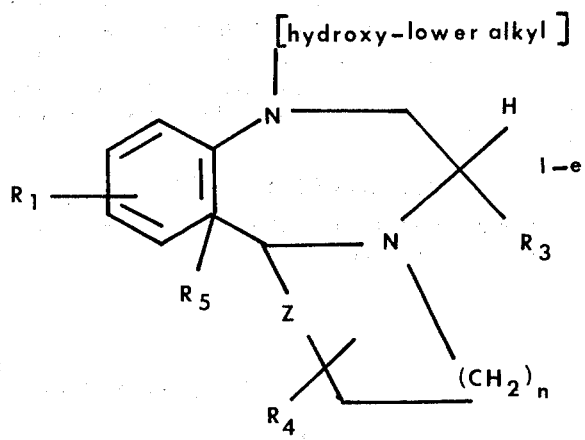

I-e wherein Z, n, $R_1$, and $R_3$–$R_5$ are as described above.

Yet another particular aspect of the present invention relates to compounds of formula I above wherein A represents the group

Z is oxygen, and n, $R_1$, $R_3$, $R_4$, and $R_5$ are as described above; or

Z is oxygen, $R_4$ is the group —$CH_2X$ where X is chlorine, bromine, lower alkoxy-lower alkyl or di-lower alkylamino and $R_1$, $R_3$, $R_5$, and n are as described above; or

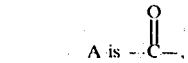

Z is oxygen, $R_5$ is pyridyl, and $R_1$, $R_3$, $R_4$ and n are as described above.

Compounds of formula I above wherein the hetero atom Z is oxygen and n is 1 are conveniently prepared by reacting a 4,5-unsaturated 1,4-benzodiazepine of the following formula

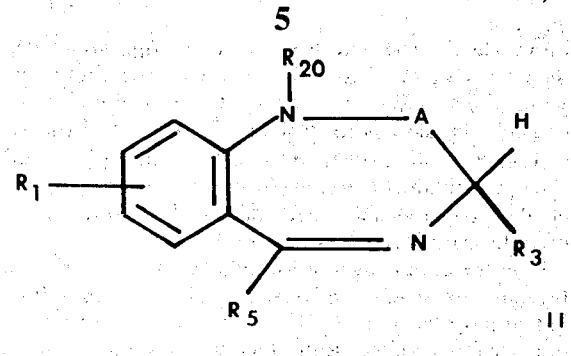

wherein $R_1$, $R_3$, $R_5$ and A are as described above and $R_{20}$ is hydrogen or hydroxy-lower alkyl with an epoxide compound of the formula

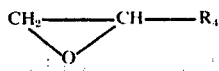   III wherein $R_4$ is as described above in the presence of an acidic agent, such as, for example, an aprotic acid, e.g., aluminum chloride, stannic chloride, zinc chloride, titanium tetrachloride, boron trifluoride, etc.; or p-toluene sulfonic acid, benzene sulfonic acid, and the like. The most preferred acidic agents for the purposes of this invention are aluminum chloride and stannic chloride. Examples of compounds of formula III useful in this invention include ethylene oxide, 1,2-propylene oxide, 1-chloro-2,3-epoxy propane, etc.

The reaction whereby compounds of formula I above wherein Z is oxygen and $n$ is 1 are prepared from the compounds of formulae II and III is conveniently conducted in the presence of an anhydrous inert organic solvent. Suitable inert organic solvents for this purpose include, for example, aromatic hydrocarbons such as benzene, toluene, xylene, etc.; ethers, such as tetrahydrofuran and diethyl ether, or carbon di-sulfide. This reaction may be carried out at a temperature in the range of from about −10° to the reflux temperature of the reaction medium, most preferably from 10° to the reflux temperature. The selection of temperatures is not critical for the purpose of the present invention and will, of course, depend upon the characteristics of the compounds selected as reagents, the solvent medium employed and the nature of the acidic agent used.

The compounds of formula II above are known or can be prepared in analogy to the preparation of the known compounds.

It should be noted that compounds of formula III above may, in addition to forming the heterocyclic ring between the 4 and 5 positions of the benzodiazepine moiety upon reaction with the compound of formula II, also react with the nitrogen atom in the 1-position of the compounds of formula II when the nitrogen is unprotected, that is when $R_{20}$ is hydrogen. Thus, the reaction of a compound of formula II wherein $R_{20}$ is hydrogen with a compound of formula III can result in a mixture of compounds, the first showing no substitution on the 1-nitrogen and the second showing hydroxy-lower alkyl substitution of the 1-nitrogen. For example, if a compound of formula II wherein $R_{20}$ is hydrogen is reacted with a compound of formula III wherein $R_4$ is hydrogen, i.e. ethylene oxide, one is able to isolate from the reaction mixture both the corresponding tricyclic compound wherein the 1-nitrogen is unsubstituted and the corresponding compound of formula I above wherein the 1-nitrogen is substituted with a β-hydroxy ethyl group. By controlling the reaction conditions there can be obtained high yields of the desired compounds of formula I wherein the 1-nitrogen bears a hydroxy-lower alkyl substituent. Thus, for example, if the reaction is conducted using an excess of the compound of formula III, the desired compound of formula I can be obtained in high yields. Likewise, the choice of the aprotic acid used as the catalyst will also control the yields obtained. Thus, aluminum chloride and stannic chloride are the preferred acid catalysts because they promote the production of the desired compounds of formula I above in high yield. In the most preferred embodiment of the present invention, aluminum chloride is used as the acid catalyst.

It would appear that when a compound of formula III is reacted with a compound of formula II, the $R_4$ bearing carbon atom can be attached relative to the benzodiazepine ring in one of two alternate positions, depending upon the point where the epoxide ring cleaves during the reaction. However, experimentation has shown that the epoxide ring evidences a propensity to favor cleavage between the oxygen and the unsubstituted carbon atom. Thus, when cleavage occurs at this point, the carbon atom bearing the $R_4$ substituent is bonded to the oxygen atom in the heterocyclic ring.

Thus, the reaction between the compounds of formulae II and III as described above produces the compounds of Formula I wherein Z is oxygen, n is 1, and the $R_4$ substitutent is joined to the 2-position of the heterocyclic ring, i.e., compounds of the formula

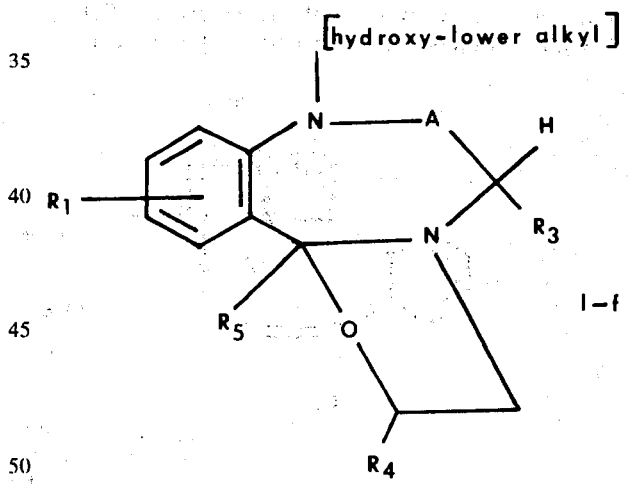

wherein $R_1$, $R_3$–$R_5$ and A are as described above.

In a further process aspect of the present invention, compounds of formula I above are conveniently prepared by reacting a corresponding 2-substituted aminophenyl ketone of the formula

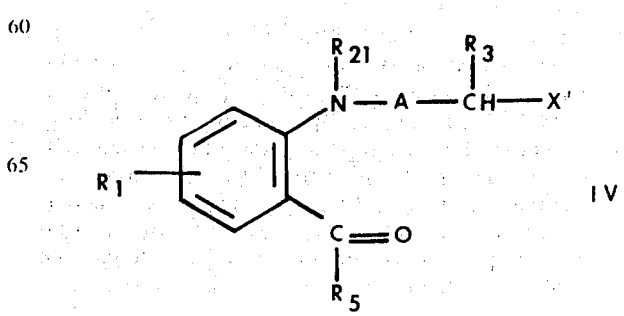

wherein $R_1$, $R_3$, $R_5$ and A are as described above, $X'$ is chlorine, bromine or iodine and $R_{21}$ is hydrogen or the group $-(CH_2)m-OR_{22}$ wherein $m$ is an integer from 1–7 and $R_{22}$ is any suitable protecting group with a diamine or aminoalkanol of the general formula

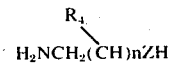     V wherein $R_4$, n and Z are as described above.

The reaction between the compounds of formulae IV and V above is conducted in a reaction medium containing a base and an inert organic solvent at a temperature in the range of from about 25°C to the reflux temperature of the reaction medium, preferably at about the reflux temperature. Suitable bases for the purposes of this invention are inorganic bases, such as sodium acetate, and organic bases such as the tertiary amines, for example, trialkylamines, with triethylamine and pyridine being preferred. A variety of organic solvents are useful for the purposes of this invention. Among these suitable solvents are aromatic hydrocarbons, such as benzene, toluene, xylene, etc.; high boiling ethers, such as tetrahydrofuran and dioxane; and amides, such as dimethylformamide, diethylformamide and the like. Examples of compounds of formula V useful in this invention include 2-aminoethanol, ethylene-diamine, 3-aminopropanol, etc.

The compounds of formulae IV and V above are readily prepared in a manner known in the art. It should be noted that in preparing the compounds of formula IV above wherein $R_{21}$ is the group $-(CH_2)_m-OR_{22}$, i.e. in preparing compounds of the formula

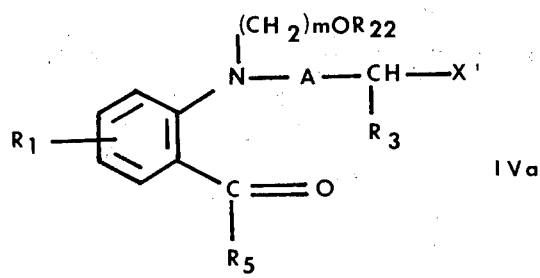     IVa wherein $R_1$, $R_3$, $R_5$, $R_{22}$, m and $X'$ are as described above it is expedient to first protect the hydroxyl group of the hydroxy-lower alkyl substituent present in the ketone starting material before indtroducing the

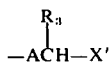

substituent, A, $R_3$ and $X'$ being defined as above, into the molecule. By so-protecting the hydroxyl group with the protecting group identified above as $R_{22}$ one can avoid unwanted side reactions and unwanted side products which of necessity render the reaction less efficient. Suitable protecting groups for this purpose include the acyl moiety of a lower alkanoic acid such as acetyl, propionyl and the like and carbobenzoxy. Following preparation of the formula IV compound and completion of the reaction between the compounds of Formulae IV and V above, the protecting group can then be split off. The splitting off of the protecting group can be effected by conventional techniques, for example, by alkaline hydrolysis. This alkaline hydrolysis is expediently carried out in the presence of an inert solvent. Suitable bases include alkali-hydroxides or alkaline earth metal hydroxides, such as sodium hydroxide, calcium hydroxide and the like.

If, in the compounds of formula IV, $X'$ is chlorine or bromine, the reaction mixture may also contain sodium iodide in order to exchange the $X'$ substitutent for the more reactive iodine atom which then is removed in the ensuing reaction.

The compounds of formula I wherein the hetero atom

and $R_6$ is lower alkyl or acyl are prepared from the corresponding compounds of formula I wherein

and $R_6$ is hydrogen by conventional alkylation or acylation procedures. By controlling the reaction conditions alkylation or acylation can be accomplished on the nitrogen of the heterocyclic ring without affecting other vulnerable positions on the benzodiazepine moiety.

The reaction path described above for the cyclization process to prepare compounds of formula I is believed to proceed via an intermediate of the following proposed structure

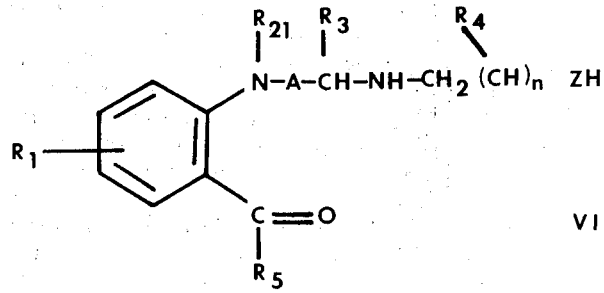     VI wherein R, $R_3$–$R_5$, $R_{21}$, A, Z and $n$ are as described above which need not be isolated from the reaction mixture as it cyclizes to the desired compounds of formula I under the reaction conditions employed. By using less energetic reaction conditions, the compounds of the formula VI can be isolated and subsequently cyclized to the desired product. However, in a preferred embodiment, the intermediate is not isolated but is permitted to cyclize in the reaction medium in which it is prepared.

In a further process aspect of the present invention, the hydroxy-lower alkyl group in the 1-position of the compounds of formula I above can be introduced onto the 1-nitrogen after formation of the tricyclic compounds. For example, if the $R_{20}$ substituent in a compound of formula II is hydrogen, the reaction of said compound with a compound of formula III may produce the corresponding tricyclic compound wherein the 1-nitrogen is unsubstituted. Further, if the $R_{21}$ substituent in a compound of formula IV is hydrogen, reaction of this compound with a compound of formula V and cyclization of the resulting intermediate will produce the corresponding tricyclic compound wherein the 1-nitrogen is unsubstituted. In either case, the desired compound of formula I above can be prepared by introducing the hydroxy-lower alkyl group into the molecule after formation of the tricyclic compound. The hydroxy-lower alkyl group can be introduced into the 1-unsubstituted tricyclic compound by reacting said compound with a suitable alkylating agent. Thus, one can prepare a compound of formula I above by first preparing the 1-sodio derivative of a compound of the formula

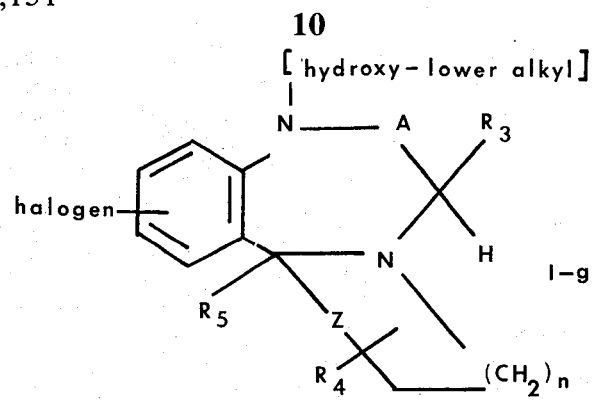

wherein $R_3$–$R_5$, A, Z and $n$ are as described above may be prepared by reacting the 1-sodio derivative of a compound of the formula

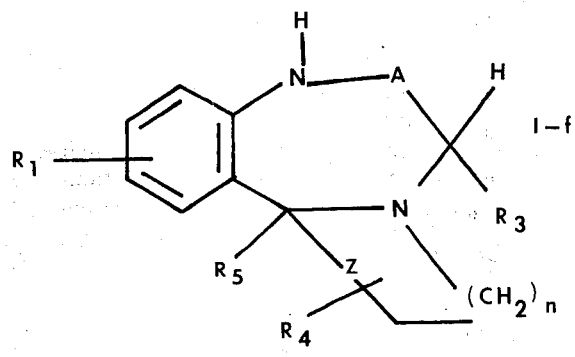

wherein $R_1$, $R_3$–$R_5$, A, Z and $n$ are as described above and without isolation reacting said 1-sodio derivative with a suitable alkylating agent such as a halo-lower alkanol. Representative of such alkylating agents are 2-bromoethanol, 3-bromopropanol and the like.

The 1-sodio derivative of a compound of formula I-f above can be prepared by treating said compound with a sodium lower alkoxide, such as sodium methoxide or with sodium hydride. This reaction is expediently effected in the presence of an inert organic solvent such as dimethylformamide (DMF), aromatic hydrocarbons, i.e. benzene, toluene and the like, with DMF being the preferred solvent. For the purposes of this reaction, temperatures above and below room temperature may be employed. In a preferred embodiment temperatures between about 0° and 10°C. are utilized.

The alkylation of the 1-sodio derivative of a compound of formula I-f above is expediently effected in the presence of an inert solvent such as DMF, aromatic hydrocarbons, i.e., benzene, toluene and the like, with DMF being the preferred solvent. This alkylation reaction may be effected using temperatures above and below room temperature, with temperatures between about 50°C and room temperature being preferred.

In a further process aspect of the present invention, a compound of formula I above wherein $R_1$ is halogen i.e., a compound of the formula

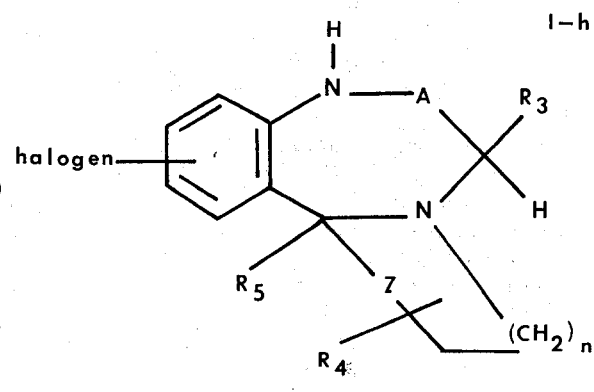

wherein $R_3$–$R_5$, A, Z and $n$ are as described above with a compound of the formula

X—(CH$_2$)$_m$COO-lower alkyl      VII wherein X is a halogen atom selected from the group consisting of chlorine, bromine and iodine and $m$ is a whole integer from 1–7 and without isolation, reducing the ester derivatives so-obtained with a suitable reducing agent such as lithium aluminum hydride.

Representative of the compounds of formula VII suitable for the process are ethyl bromoacetate, ethyl 3-bromopropionate, and the like. The 1-sodio derivative of the compound of formula I-h can be prepared, as described hereinbefore. The alkylation reaction is expediently effected in the presence of an inert solvent such as DMF.

The tricyclic benzodiazepine derivatives of formula I above are useful as pharmaceuticals and are characterized by activity as sedative, muscle relaxant and anticonvulsant agents. These compounds can be used in the form of conventional pharmaceutical preparations; for example, the aforesaid compounds can be mixed with conventional organic or inorganic, inert pharmaceutical carriers suitable for parenteral or enteral administration such as for example, water gelatin, lactose, starch, magnesium stearate, talc, vegetable oil, gums, polyalkylene glycols, Vaseline or the like. They can be administered in conventional pharmaceutical forms, e.g., solid forms, for example, tablets, dragees, capsules suppositories or the like, or in liquid forms, for example, solutions, suspensions or emulsions. Moreover, the pharmaceutical compositions containing compounds of this invention can be subjected to conventional pharmaceutical expedients such as sterilization, and can contain conventional pharmaceutical excipients such as preservations, stabilizing agents, wetting agents, emulsifying agents, salts for the adjustment of osmotic pressure, or buffers. The compositions can also contain other therapeutically active materials.

A suitable pharmaceutical dosage unit can contain from about 1 to about 500 mg of the aforesaid compounds of formula I; with a dosage range of from about 1 mg to about 100 mg being the preferred oral administration and a dosage range of from about 1 mg to about 50 mg being preferred for patenteral administration. However, for any particular subject, the specific dosage regimen should be adjusted according to individual need and the professional judgement of the person administering or supervising the administration of the aforesaid compounds. It is to be understood that the dosages set forth herein are exemplary only and that they do not, to any extent, limit the scope or practice of this invention.

The term "dosage unit" as employed throughout this specification refers to pharmaceutically discrete units suitable as unitary dosages for mammalian subjects each containing a predetermined quantity of active material calculated to produce the desired therapeutic effect in association with the required pharmaceutical diluent, carrier or vehicle.

The following examples are illustrative, but not limitative of this invention. All temperatures given are in degrees centigrade, unless indicated otherwise.

EXAMPLE 1

Preparation of
10-chloro-2,3,5-11b-tetrahydro-11b-phenyloxazolo
[3,2-d] [1,4]benzodiazepin-6-(7H)-one

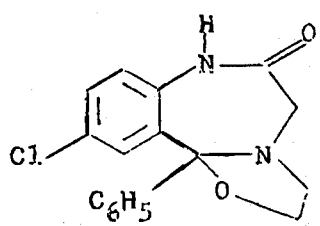

To 5 gm. (18.5 mole) of 7-chloro-1,3-dihydro-5-phenyl-2H-1,4-benzodiazepin-2-one in 90 ml. of dry benzene was added 5.0 g. (37 mmole) of aluminum chloride. The reaction mixture was stirred 6 hours at reflux, cooled to room temperature and treated with 4.4 g. (0.1 mole) of ethylene oxide. The reaction mixture was stirred 18 hours, the benzene was then removed and the residue was treated with aqueous ammonium hydroxide and 100 ml. of methylene chloride. The resulting precipitate was removed by filtration. The organic layer was then separated, washed with brine, dried and the solvent evaporated to yield a residue which was crystallized from ether and recrystallized from methylene chloride-hexane to give the above-titled product as colorless prisms, m.p. 125°–135° and then resetting, m.p. 173°–177°.

EXAMPLE 2

Preparation of
10-chloro-7-(2-hydroxyethyl)-2,3,5,11b-tetrahydro-11b-phenyloxazolo[3,2-d]
[1,4]benzodiazepin-6-(7H)-one

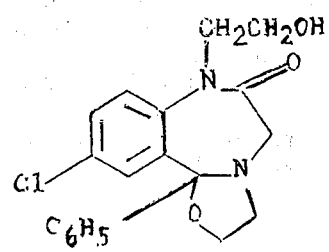

The filtrates from Example 1 above were dissolved in methylene chloride and chromatographed over silica gel (200 g.) with methylene chloride (300 ml.) and with 700 ml. of ethyl acetate. The ethyl acetate fraction was evaporated to dryness and crystallized from ether. Recrystallization from methylene chloride-hexane gave the above-titled product as colorless prisms, m.p. 134°–137°.

EXAMPLE 3

Preparation of
10-chloro-11b-(2-fluorophenyl)-2,3,5,11b-tetrahydrooxazolo[3,2-d] [1,4]benzodiazepin-6-(7H)-one

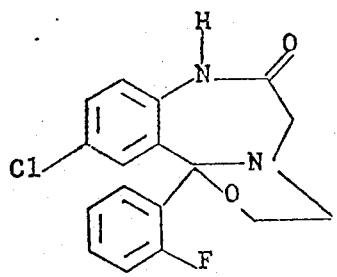

To 15 g. (51.9 mmole) of 7-chloro-5-(2-fluorophenyl)-1,3-dihydro-2H-1,4-benzodiazepin-2-one in 150 ml. of dry benzene, 9 g. (67.7 mmole) of aluminum chloride was added and stirring was continued 15 minutes. The reaction mixture was cooled in an ice bath and 8.8 g. (0.2 mole) of ethylene oxide was added dropwise. After 18 hours of stirring at room temperature, the reaction mixture was heated to 40° for 1 hour and then cooled to room temperature and treated with 5 g. (37.6 mmole) of aluminum chloride, followed by 4.4 g. (0.1 mole) of ethylene oxide. The reaction mixture was heated 4 hours at 45°–50° and then evaporated to dryness. ethylene chloride, ice and ammonium hydroxide were added and the solid removed by filtration. The filtrate was separated and the organic phase reduced to dryness in vacuo. The residue was dissolved in dilute hydrochloric acid and the pH of the solution adjusted to 5 with ammonium hydroxide. The acidic solution was washed with ether, made basic and extracted with methylene chloride. The organic phase was washed with brine, dried and evaporated to dryness. Recrystallization from methylene chloride-hexane gave the above-titled product as colorless rods, m.p. 183°–184°.

EXAMPLE 4

Preparation of 10-chloro-11b-(2-fluorophenyl)-7-(2-hydroxyethyl)-2,3,5,11b-tetrahydrooxazole[3,2-d] [1,4]benzodiazepin-6(7H)-one

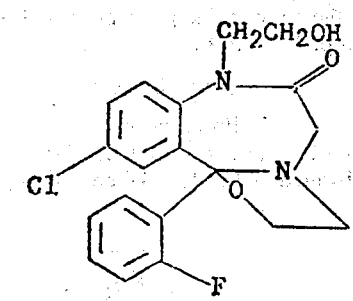

The ether wash in Example 3 of the said solution at pH 5 was evaporated to dryness, dissolved in methylene chloride and chromatographed over 200 g. of silica gel with methylene chloride and ethyl acetate which fractions were combined and the solvents removed to give crude product. Recrystallizations from methylene chloride petroleum ether gave the above-titled product as colorless plates, m.p. 147°–151°.

EXAMPLE 5

Preparation of 10-chloro-7-methyl-2,3,5,11b-tetrahydro-11b-phenyloxazolo[3,2-d] [1,4]benzodiazepin-6-(7H)-one

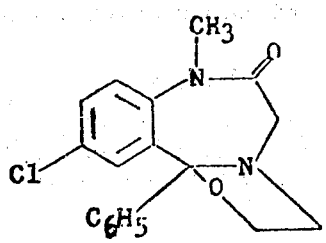

Method A

A mixture of 100 ml. of dried benzene and 5.0 g. of aluminum chloride under a dry ice-acetone filled condenser was stirred and treated with 10.0 g. (35 mmole) of 7-chloro-1,3-dihydro-1-methyl-5-phenyl-2H-1,4-benzodiazepin-2-one giving a yellow solid. Stirring was continued for 20 minutes and after the addition of 35 ml. of hexane, the mixture was cooled in an ice-bath. Upon the addition of 7 ml. of ethylene oxide, the yellow solid dissolved. The reaction mixture was warmed to room temperature and was stirred overnight. The benzene solution was repartitioned between methylene chloride and iced aqueous ammonium hydroxide. Filtration removed a large portion of the aluminum salts and the organic layer was separated, washed with water, dried and evaporated. The resultant residue was washed with ether to give the above-titled product as colorless crystals, m.p. 179°–184°. Two recrystallizations from methylene chloride-hexane gave colorless rods, m.p. 182°–184°.

Method B

A solution of 6.4 g. (20 mmole) of 2-(2-chloro-N-methylacetamido)-5-chlorobenzophenone, 12.2 g. (200 mmole) of 2-aminoethanol, 50 ml. of triethylamine and 300 ml. of ethanol was stirred overnight at reflux. The reaction mixture was concentrated to a semi-solid residue, from which the above-titled product was obtained as an ether insoluble crystalline material, m.p. 180°–183°.

EXAMPLE 6

Preparation of 10-chloro-2,7-dimethyl-2,3,5,11b-tetrahydro-11b-phenyloxazolo[3,2-d] [1,4]benzodiazepin-6(7H)-one (2,11b cis)

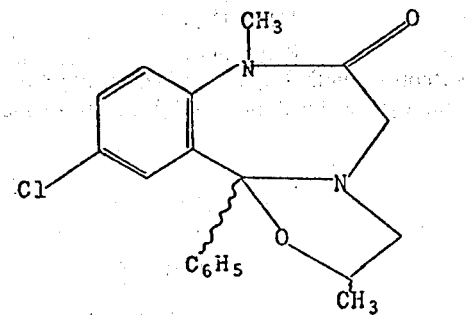

A mixture of 10.0 g. (35 mmole) of 7-chloro-1,3-dihydro-1-methyl-5-phenyl-2H-1,4-benzodiazepin-2-one, 6.7 g. of aluminum chloride, 300 ml. of benzene and 30 ml. of hexane was chilled in an ice-bath and was treated with 10 ml. of propylene oxide. The reaction mixture was warmed to room temperature and was stirred overnight. Work-up as in Method A, Example 5, yielded a mixture of the epimers of 10-chloro-2,7-dimethyl-2,3,5,11b-tetrahydro-11b-phenyloxazolo[3,2-d] [1,4]benzodiazepin-6(7h)-one. A solution of 1.0 g. of this mixture was stirred overnight at 80° in 25 ml. of boron trifluoride etherate. The reaction mixture was poured carefully into ice water and made basic with ammonium hydroxide. The mixture was extracted with chloroform, water washed, dried and concentrated to a solid residue. Three recrystallizations from methylene chloride-hexane gave the abovetitled isomer, m.p. 142°–143°.

EXAMPLE 7

Preparation of 10-chloro-2-chloromethyl-2,3,5,11b-tetrahydro-7-methyl-11b-phenyloxazolo[3,2-d][1,4]benzodiazepin-6(7H)-one

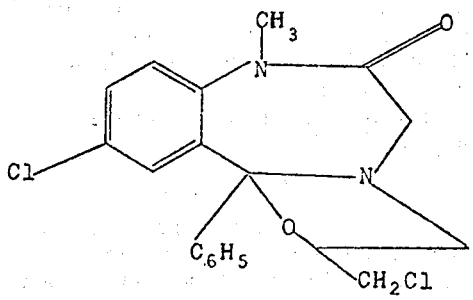

A mixture of 10 g. (35 mmole) of 7-chloro-1,3-dihydro-1-methyl-5-phenyl-2H-1,4-benzodiazepin-2-one, 10 g. of aluminum chloride, and 200 ml. of dried benzene was treated with 30 ml. of 1-chloro-2,3-epoxypropane in 100 ml. of benzene. The reaction mixture was stirred overnight. Work-up as in Method A, Example 5, above gave 32 g. of a crude oil. The oil was dissolved in benzene, filtered over Florisil, evaporated to dryness and crystallized from ether-petroleum ether to give the above-titled product as colorless needles, m.p. 140°–142°.

EXAMPLE 8

Preparation of 10-chloro-7-methyl-2,3,5,6,7,11b-hexahydro-11b-phenyloxazolo[3,2-d][1,4]benzodiazepine

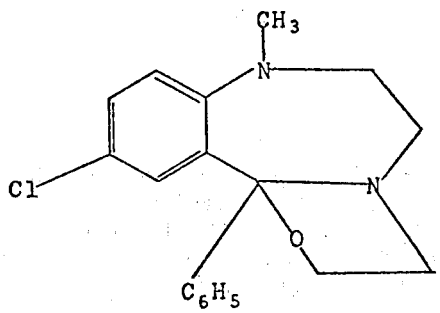

Method A

A mixture of 12.5 g. (46 mmole) of 7-chloro-2,3-dihydro-1-methyl-5-phenyl-1H-1,4-benzodiazepine hydrochloride, 5.0 g. of aluminum chloride, 200 ml. of benzene and 30 ml. of hexane was stirred for 20 minutes, chilled in an ice-bath and then treated with 7.0 ml. of ethylene oxide. The reaction mixture was warmed to room temperature and stirred overnight. The benzene was removed by evaporation and the residue was partitioned between methylene chloride and dilute ammonium hydroxide. The solid was removed by filtration and the organic layer washed with water, dried and evaporated to give an orange oil. Upon standing, the oil crystallized and the resultant solid was recrystallized from hexane to give the above-titled product. An analytical sample was obtained as colorless prisms, m.p. 109°–110°, by recrystallization from ether.

Method B

A solution of 5.6 g. (18.2 mmole) of 5-chloro-2-(2-chloroethylmethylamino)benzophenone, 5.0 g. of sodium iodide, 50 ml. of 2-aminoethanol, 50 ml. of triethylamine and 100 ml. of ethanol was heated at reflux for 17 hours. The reaction mixture was poured into ice water and was extracted with methylene chloride. The organic phase was washed with water, dried and evaporated to an oil. The oil was cooked out with petroleum ether and the above-titled product crystallized from the solvent, m.p. 107°–109°.

EXAMPLE 9

Preparation of 10-chloro-1,2,3,5,7,11b-tetrahydro-7-methyl-11b-phenyl-6H-imidazo[1,2-d]1,4]benzodiazopin-6-one

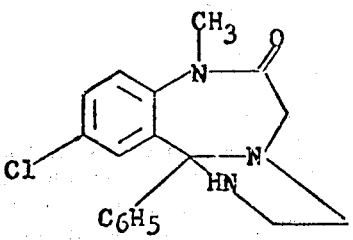

A solution of 6.4 g. (20 mmole) of 2-(2-chloro-N-methylacetamido)-5-chlorobenzophenone, 12.0 g. (0.2 mole) of ethylenediamine, 50 ml. of triethylamine and 250 ml. of ethanol was heated at reflux for 20 hours. The reaction mixture was concentrated to a residue which was partitioned between ether and water. The ether layer was washed with water, dried and concentrated to a small amount of liquid which was treated with a small amount of ethanol to give upon standing the above-titled product as colorless crystals, m.p. 164°–167°.

EXAMPLE 10

Preparation of 11-chloro-3,4,6,7,8,12b-hexahydro-8-methyl-12b-phenyl-2H-[1,3]oxazino[3,2-d][1,4]benzodiazepine

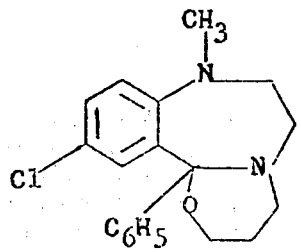

17

A solution of 5.0 g. of (16 mmole) of 5-chloro-2-(2-chloroethylmethylaminoe)benzophenone, 3.75 g. (50 mmole) of 3-aminopropanol, 50 ml. of triethylamine and 250 ml. of ethanol was stirred at reflux for 48 hours. The reaction mixture was then evaporated to a residue which was washed with water, dissolved in methylene chloride and chromatographed over a column of Florisil. The first fraction yielded the recovery of 2.7 g. of starting material. Elution with acetone, ethanol, methanol and finally with ammonial methanol gave a compound of very low Rf on fluorescent silica eluted with ethanol. Crystallization from acetone and recrystallizations from ether-petroleum ether gave the above-titled product as colorless prisms, m.p. 142°–144°.

EXAMPLE 11

Preparation of 10-chloro-2,3,5,6,7,11b-hexahydro-7-methyl-11b-phenyl-1H-imidazo[1,2-d][1,4]benzodiazepine

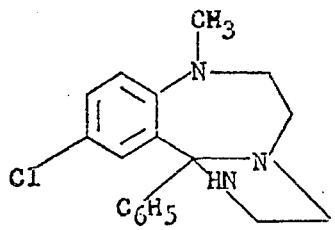

A solution of 5.0 g. (16 mmole) of 5-chloro-2-(2-chloroethylmethylamino)benzophenone, 3.0 g. (50 mmole) of ethylenediamine, 50 ml. of triethylamine and 250 ml. of ethanol was stirred at reflux for 48 hours. The solvents were removed by evaporation and the residue containing starting material and the product was washed with water, chromatographed over Florisil, and recrystallized from petroleum ether to give the above-titled product as yellow prisms, m.p. 100°–102°.

EXAMPLE 12

Preparation of 10-chloro-2,3,5,11b-tetrahydro-2-methyl-11b-phenyloxazolo[3,2-d][1,4]benzodiazepin-6(7H)-one (2,11b trans)

A solution of 67 g. (0.19 mole) of 2-(2-bromoacetamido)-5-chloro-benzophenone, 500 ml. of xylene, 15.7 g. (0.21 mole) of 1-amino-2-propanol and 25 ml. of triethylamine was stirred at reflux for 20 hours. The reaction mixture was concentrated in vacuo to a residue which was partitioned between methylene chloride and water. The organic layer was washed with water, dried and concentrated to an oil which was crystallized from ethyl acetate to give 18.3 g. of a colorless solid, m.p. 181°–184°. Thin layer chromatography on Eastman alumina plates with an eluant of 3 parts of hexane and 2 parts of ethyl acetate revealed the presence of two compounds. The product was dissolved in chloroform and chromatographed over Woelm neutral alumina I. A mixture concentrated in the above-titled product (the faster of the two compounds) was collected in 30% ethyl acetate-70% hexane. Recrystallizations from methylene chloride gave colorless prisms, m.p. 188°–189°.

EXAMPLE 13

Preparation of 10-chloro-2,3,5,11b-tetrahydro-2-methyl-11b-phenyloxazolo[3,2-d][1,4]benzodiazepin-6(7H)-one (2,11b cis)

A 1.0 g. sample (0.3 mmol) of the two-compound mixture obtained in Example 12 was stirred 17 hours at 80° in a solution with 25 ml. of boron trifluoride etherate. The reaction mixture was poured over 200 g. of ice and was carefully treated with ammonium hydroxide to give a pH of 8. The resultant solid was removed by filtration and was air dried to give the above-titled product. Two recrystallizations from chloroform-hexane gave colorless prisms, m.p. 172°–174°.

EXAMPLE 14

Preparation of a mixture of 10-chloro-2,3,5,11b-tetrahydro-2-methyl-11b-phenyloxazolo[3,2-d][1,4]benzodiazepin-6(7H)-one (2,11b cis) and 10-chloro-2,3,5,11b-tetrahydro-2-methyl-11b-phenyloxazolo[3,2-d][1,4]benzodiazepin-6(7H)-one (2,11b trans)

Method A

To a solution of 35.26 g. (0.1 mole) of 2-(2-bromoacetamido)-5-chlorobenzophenone, 100 ml. of triethylamine and 600 ml. of ethanol, 22.5 g. (0.3 mole) of 1-amino-2-propanol was added. The reaction mixture was stirred at room temperature for 65 hours. The solvent was removed in vacuo and the residue partitioned between water and ethyl acetate. The organic layer was dried and concentrated to give a colorless oil. An ether solution of the oil was treated with dry hydrogen chloride to form the hydrochloride salt which was recrystallized from ethanol to give colorless prisms of 5-chloro-2[2-(2-hydroxypropylamino)acetamido]benzophenone, m.p. 194°–195°.

A pyridine solution of 8.0 g. (23 mmol) of 5-chloro-2[2-(2-hydroxypropylamino)acetamido]benzophenone was stirred 17 hours at reflux in the presence of 0.5 g. of pyridine hydrochloride. The reaction mixture was concentrated in vacuo to a residue which was crystallized from ethanol as colorless crystals, m.p. 184°–185°. The product is a mixture of the above-titled compounds in about equal portions.

In a similar fashion, 5-chloro-2[2-(2-hydroxypropylamino)acetamido]benzophenone could be dehydrated to give a mixture of the same two compounds by heating at reflux 72 hours in ethanol or by heating 65 hours at reflux in xylene.

Method B

A solution of 5.4 g. (20 mmol) of 7-chloro-1,3-dihydro-5-phenyl-2H-1,4-benzodiazepin-2-one and 20 mmol of stannic chloride in 300 ml. of dry benzene was treated with 60 mmol of propylene oxide and stirred under dry nitrogen for 22 hours at 80°. The reaction mixture was concentrated in vacuo to a residue which was partitioned between methylene chloride and ammonia. The organic phase was washed with water, dried and concentrated to give a crystalline residue. Recrystallization from ethyl acetate gave colorless prisms, m.p. 178°–183°, of a mixture of the above-titled compounds.

Similarly, this reaction was effected in benzene solution using aluminum trichloride, titanium tetrachloride or boron trifluoride etherate as catalysts.

Method C

Following the procedures set forth in Examples 12 and 13, the mixtures obtained in Methods A and B can be separated in order to isolate 10-chloro-2,3,5,11b-tetrahydro-2-methyl-11b-phenyloxazolo[3,2-d][1,4]benzodiazepin-6(7H)-one (2,11b cis) and 10-chloro-2,3,5,11b-tetrahydro-2-methyl-11b-phenyloxazolo[3,2-d][1,4]benzodiazepin-6(7H)-one (2,11b trans).

EXAMPLE 15

Preparation of
10-chloro-2,3,5,11b-tetrahydro-3-methyl-11b-phenyloxazolo[3,2-d][1,4]benzodiazepin-6(7H)-one (3,11b cis)

A mixture of 79.4 g. (255 mmole) of 2-(2-bromoacetamido)-5-chlorobenzophenone, 25 g. of 2-aminopropanol hydrochloride, 95 ml. of triethylamine and 500 ml. of ethanol was stirred overnight at room temperature, and then at reflux for 5 hours. The solution was concentrated under reduced pressure to a residue which was partitioned between ether and water. The organic layer was washed with water, dried and treated with hydrogen chloride to give 18 g. of a colorless solid. Recrystallizations from ethanol-ether gave prisms of 5-chloro-2-[2-(1-hydroxy-2-propylamino)acetimido]-benzophenone, hydrochloride, m.p. 183°–186°.

A solution of 5 g. (13 mmol) of the free base 5-chloro-2[1-hydroxy-2-propylamino)acetamido]benzophenone was heated 16 hours in refluxing pyridine (100 ml.). The solution was concentrated in vacuo to an oil which was chromatographed over silica. The first material taken in 60% ethyl acetate, 40% hexane was 2-amino-5-chlorobenzophenone. The next material eluted was combined to give 10-chloro-2,3,5,11b-tetrahydro-3-methyl-11b-phenyloxazolo[3,2-d][1,4]benzodiazepin-6(7H)-one (3,11b cis) which was recrystallized 3 times to give colorless prisms, m.p. 88°–96°. Sublimation under reduced pressure gave a colorless solid, m.p. 84°–98°.

EXAMPLE 16

Preparation of
10-chloro-11b-(2-chlorophenyl)-2,3,5,11b-tetrahydrooxazolo[3,2-d][1,4]benzodiazepin-6(7H)-one A suspension of 4.3 g. (0.0328 M) of aluminum chloride in 200 ml. of dry benzene under nitrogen was treated with 5.0 g. (0.0164 M) of 7-chloro-5-(2-chlorophenyl)-1,3-dihydro-2H-1,4-benzodiazepin-2-one and the mixture was stirred in an ice bath for 20 min. when 2.2 g. (0.0492 M) of ethylene oxide was added and after 18 hr. at room temperature, an additional 2.2 g. of ethylene oxide was added. After 3 hr., the mixture was heated under reflux for 10 min., then evaporated to dryness.

The residue was made basic with ammonium hydroxide, dichloromethane (100 ml.) was added and the mixture was filtered. The organic layer was separated, washed with saturated brine, dried over anhydrous sodium sulfate and evaporated to dryness. The residue was crystallized from ether and recrystallized from a mixture of dichloromethane and petroleum ether to give 10-chloro-11b-(2-chlorophenyl)-2,3,5,11b-tetrahydrooxazolo[3,2-d][1,4]benzodiazepin-6(7H)-one as white prisms, m.p. 213°–216°.

EXAMPLE 17

Preparation of
10-chloro-11b-(2-chlorophenyl)-7-methoxymethyl-2,3,5,11b-tetrahydrooxazolo[3,2-d][1,4]benzodiazepin-6(7H)-one A solution of 2.8 g. of 10-chloro-11b-(2-chlorophenyl)-2,3,5,11b-tetrahydrooxazolo[3,2-d][1,4]benzodiazepin-6(7H)-one in 50 ml. of dimethylformamide was cooled to −10° and treated with 0.65 g. of sodium methoxide. After stirring for 5 minutes, the mixture was cooled to −40° and 1 ml. of chlorodimethyl ether was added. The cooling bath was removed and when the temperature had reached 0° the reaction mixture was poured into 300 ml. of ice-water. The precipitated material was collected by suction and dissolved in methylene chloride. The solution was dried over sodium sulfate, filtered and evaporated. The residue was crystallized from a mixture of ether and hexane to give, after recrystallization from ethanol, 10-chloro-11b-(2-chlorophenyl)-7-methoxymethyl-2,3,5,11b-tetrahydrooxazolo[3,2-d][1,4]benzodiazepin-6(7H)-one as white prisms, m.p. 144°–147°.

EXAMPLE 18

Preparation of Ethyl
7-chloro-1,3-dihydro-5-phenyl-2H-1,4benzodiazepin-2-one-3carboxylate A solution of 50 g. of sodium nitrite is added dropwise to a solution of 34.6 g. of ethyl 2'-benzoyl-4'-chloro-malonanilate in 250 ml. of glacial acetic acid. After 1½ hours stirring at room temperature, the oxime crystallizes out and is filtered off by suction, washed with water and dried in vacuum. Ethyl 2'-benzoyl-4'-chloro-mesoxalanilate 2-oxime, m.p. 98°–105° is obtained.

Water is added dropwise to the filtrate with stirring whereby further oxime crystallizes out.

According to thin layer chromatogram, the crude product consists of a mixture of the two stereoisomeric oximes. These may be separated by chromatography on Kieselgel with 20% acetic ester in methylene chloride. The first eluded isomer melts at 115°–117° after crystallization from alcohol-water. The oxime eluted later shows a m.p. of 131°–132° after crystallization from ether-hexane.

A solution of 2 g. of ethyl 2'-benzoyl-4'-chloro-mesoxalanilate 2-oxime in 40 ml. of methylene chloride is treated with 2 g. of zinc dust. 4 ml. of glacial acetic acid are added dropwise within 5 minutes with stirring. After the addition, the mixture is stirred at room temperature for 1 hour. The reaction mixture is filtered and the filtrate evaporated. The residue is boiled under reflux for 2 hours in 20 ml. of benzene and 2 ml. of glacial acetic acid. The reaction mixture is washed out with 10% soda solution, dried over sodium sulphate and evaporated. Crystallization of the residue from alcohol yields ethyl 7-chloro-1,3-dihydro-5-phenyl-2H-1,4-benzodiazepin-2-one-3-carboxylate, m.p. 232°–234°. Further material crystallizes from the mother liquor.

EXAMPLE 19

Preparation of
10-chloro-11b-phenyl-2,3,5,11b-tetrahydrooxazolo[3,2-d] [1,4]benzodiazepin-6(7H)-one-5-carboxylic acid ethyl ester To a solution of 3.1 g. (0.0118 M) of stannic chloride in 35 ml. of dry ethylene dichloride under nitrogen was added 1.5 g. (0.00438 M) of 7-chloro-1,3-dihydro-2-oxo-5-phenyl-2H-1,4-benzodiazepine-3-carboxylic acid ethyl ester. The reaction was stirred in an ice bath, when a solution of 1.0 g. (0.0233 M) of ethylene oxide in 5 ml. of ethylene dichloride was added. The mixture was stirred at room temperature for 3 hr. and then made basic with mixture of ammonium hydroxide and ice. The mixture was filtered, and the filtrate was dried with anhydrous sodium sulfate and evaporated to dryness. The residue was crystallized from ether. Recrystallization from a mixture of dichloromethane and petroleum ether gave 10-chloro-11b-phenyl-2,3,5,11b-tetrahydrooxazolo[3,2-d] [1,4]benzodiazepin-6(7H)-one-5-carboxylic acid ethyl ester as white rods, m.p. 205°–207°.

EXAMPLE 20

Preparation of
10-Chloro-11b-(2-fluorophenyl)-7-(2-hydroxyethyl)-2,3,5,11b-tetrahydrooxazolo[3,2-d][1,4]benzodiazepin-6(7H)-one Method A A solution of 3.3 g (0.01 M) of 7-chloro-1-(2-hydroxyethyl)-5-(2-fluorophenyl)-1,3-dihydro-2H-1,4-benzodiazepin-2-one in 40 ml of 1,2-dichloro ethane under nitrogen was treated with 5.2 g (0.02 M) of stannic chloride with stirring. After 20 min, the mixture was cooled in an ice bath and 2.6 g (0.06 M) of ethylene oxide was added. After 1 hr at room temperature, the reaction mixture was made basic with ammonium hydroxide and filtered. The precipitate was washed with dichloromethane, and the combined filtrates were separated. The organic layer was washed with 40 ml of dilute ammonium hydroxide, dried over anhydrous sodium sulfate and evaporated to dryness. The residue was crystallized from a mixture of ether and petroleum ether and recrystallized from toluene to give the above named product as white prisms, mp 142°–147°.

Method B

A solution of 5 g (0.015 M) of 10-chloro-11b-(2-fluorophenyl)-2,3,5,11b-tetrahydrooxazolo[3,2-d][1,4]benzodiazepin-6(7H)-one in 50 ml of dry N,N-dimethylformamide under nitrogen was treated with 1.3 g (0.030 M) of a 57% dispersion of sodium hydride in mineral oil and after 30 min, 4.0 g (0.030 M) of 2-bromoethanol was added. The mixture was kept at 60° for 18 hrs, when 450 ml of water was added, followed by enough 3N hydrochloric acid to lower pH to less than 5. The mixture was extracted with dichloromethane (3 × 125 ml). The organic layers were combined, washed with saturated brine, dried over anhydrous sodium sulfate and evaporated to dryness. The residue was dissolved in ether (50 ml) and filtered through 75 g of neutral alumina. Elution with ethyl acetate and methanol gave the above named product, which was crystallized from ether to give the product as white prisms, mp 142°–147°.

EXAMPLE 21

Preparation of
11b-(2-Fluorophenyl)-2,3,5-11b-tetrahydro-10-iodo-oxazolo[3,2-d][1,4]benzodiazepin-6(7H)-one To a mixture of 5.34 g (40 mmole) of aluminum chloride and 250 ml of benzene was added 7.6 g (20 mmole) of 5-(2-fluorophenyl)-1,3-dihydro-7-iodo-2H-1,4-benzodiazepin-2-one. This mixture was then cooled in an ice bath, 10 ml (0.2 mole) of ethylene oxide was added to it and then it was stirred for 2 days at room temperature. The mixture was concentrated in vacuo and the residue shaken with methylene chloride and saturated sodium bicarbonate solution. The insoluble material was filtered off and discarded. The methylene chloride layer was separated, dried over sodium sulfate and concentrated in vacuo. The residue was crystallized with ether to give the above named product, mp 180°–184°. Recrystallization from 70% aqueous ethanol gave colorless needles, mp 193°–196°.

EXAMPLE 22

Preparation of
11b-(2-Fluorophenyl)-7-(2-hydroxyethyl)-10-iodo-2,3,5,11b-tetrahydrooxazolo[3,2-d][1,4]benzodiazepin-6(7H)-one A solution of 0.8 g (0.00187 M) of 11b-(2-fluorophenyl)-2,3,5-11b-tetrahydro-10-iodo-oxazolo[3,2-d][1,4]benzodiazepin-6(7H)-one in 25 ml of dry N,N-dimethylformamide under nitrogen was treated with 0.11 g (0.00262 M) of a 57% dispersion of sodium hydride in mineral oil. After stirring for 30 minutes in an ice bath, 0.37 g (0.00374 M) of 2-bromoethanol was added, and the reaction was heated to 115°–120° for 3 hr and at 125°–130° for 1 hr. The solvent was removed under vacuum, and the residue was dissolved in 25 ml of dichloromethane and washed with saturated brine, dried over anhydrous sodium sulfate and evaporated to dryness. The residue was heated under reflux for 15 minutes in a solution of 10 ml of triethylamine, containing 0.5 g (0.005 M) of succinic anhydride. Solvent was removed under reduced pressure and the residue was dissolved in 25 ml of dichloromethane. The half ester was extracted into 20 ml of dilute ammonium hydroxide which was then treated with 5 ml of 3N sodium hydroxide for 1 hr. The solution was extracted with 25 ml of dichloromethane, which was dried with anhydrous sodium sulfate, and evaporated. The resulting oil was crystallized from ether to give the above named product as white plates, mp 160°–165°.

EXAMPLE 23

Preparation of
11b-(2-Chlorophenyl)-10-nitro-2,3,5,11b-tetrahydrooxazolo[3,2-d][1,4]-benzodiazepin-6(7H)-one A solution of 5.2 g of (0.02 M) of stannic chloride in 60 ml of dry ethylene dichloride under nitrogen was treated with 2.9 g (0.0091 M) of 5-(2-chlorophenyl)-1,3-dihydro-7-nitro-2H-1,4-benzodiazepin-2-one. The reaction was cooled in an ice bath, and 2.6 g (0.06 M) of ethylene oxide in 10 ml of ethylene dichloride was added with stirring over an 8 min period. After 18 hr at room temperature, the solution was made basic with concentrated ammonium hydroxide and filtered. The filtrates were washed with a saturated solution of brine, dried over anhydrous sodium sulfate and evaporated to dryness. The residue was crystallized from a mixture of dichloromethane, methanol and petroleum ether to give the above named product as white rods, melting at 201°–203°.

EXAMPLE 24

Preparation of
11b-(2-Chlorophenyl)-7-(2-hydroxyethyl)-10-nitro-2,3,5,11b-tetrahydrooxazolo[3,2-d][1,4]benzodiazepin-6(7H)-one A solution of 1.5 g (0.0041 M) of 11b-(2-chlorophenyl)-10-nitro-2,3,5,11b-tetrahydooxazolo[3,2-d][1,4]benzodiazepin-6(7H)-one in 30 ml of dry N,N-dimethylformamide was treated with 0.34 g (0.008 M) of a 57% dispersion of sodium hydride in mineral oil with stirring under nitrogen. After 30 min, 1.5 g (0.012 M) of 2-bromoethanol was added and the reaction was heated to 90° for 3 hr. The solvent was removed under vacuum, and the residue was dissolved in 50 ml of dichloromethane which was then washed with 50 ml of water, 25 ml of a saturated solution of brine, dried over anhydrous sodium sulfate and evaporated to dryness. The residue was crystallized from ether, and recrystalized from a mixture of dichloromethane and methanol to give the product as pale yellow prisms, m.p. 185°–190°(dec.).

EXAMPLE 25

In an analagous manner to the procedures described in Example 24, the following compounds may be prepared using 10-chloro-11b-(2-fluorophenyl)-2,3,5,11b-tetrahydrooxazolo[3,2-d][1,4]benzodiazepin-6(7H)-one as the starting material:

10-Chloro-11b-(2-fluorophenyl)-7-(2-dimethylaminoethyl)-2,3,5,11b-tetrahydrooxazolo[3,2-d][1,4]benzodiazepin-6(7H) one, from (2-bromoethyl)dimethylamine 10-Chloro-11b-(2-fluorophenyl)-7-(3-aminopropyl)-2,3,5,11b-tetrahydrooxazolo[3,2-d][1,4]benzodiazepin-6 (7H)one, from 3-bromopropylamine 10-Chloro-11b(2-fluorophenyl)-7-(3-methylaminopropyl)-2,3,5,11b-tetrahydrooxazolo[3,2-d][1,4]benzodiazepin-6(7H)one, from (3-bromopropyl)methylamine 10-Chloro-11b-(2-fluorophenyl)-7-(2-diethylaminoethyl)-2,3,5,11b-tetrahydrooxazolo[3,2-d][1,4]benzodiazepin-6(7H)-one, from (2-bromoethyl)diethylamine

EXAMPLE 26

Preparation of
10-Chloro-11b-(2-fluorophenyl)-7-(2-hydroxyethyl)-2,3,5,11b-tetrahydrooxazolo[3,2-d][1,4]benzodiazepin-6(7H)-one A solution of 33.3g (0.1 M) of 10-chloro-11b-(2-fluorophenyl)2,3,5,11b-tetrahydrooxazolo[3,2-d][1,4]benzodiazepin-6(7H)-one in 100 ml of dry N,N-dimethylformamide was treated with 6.6g (0.138 M) of a 50 per cent dispersion of sodium hydride in mineral oil. The mixture was stirred for 0.5 hour at room temperature, was then cooled to 5°–10° and treated with a solution of 31g (0.186 M) of ethyl bromoacetate in 25 ml of dry N,N-dimethylformamide. The resulting mixture was allowed to stir at room temperature for 18 hours when 3 ml of water was carefully added. The solution was next evaporated to dryness under reduced pressure. The residue was next treated with 50 ml of toluene and evaporated to dryness. This procedure was repeated twice in order to azeotrope any remaining water or N,N-dimethylformamide. The crude ester thus obtained was dissolved in 250 ml of dry tetrahydrofuran, cooled to 0° and was treated by the portionwise addition of 1.9g (0.05 M) of lithium aluminium hydride. The cooling bath was removed and the mixture was allowed to stir for 3 hours. Enough saturated sodium bicarbonate solution was added to coagulate the solids and the mixture was filtered. The filtrates were concentrated to dryness and dissolved in dichloromethane. The solution was washed with 1N hydrochloric acid, water, saturated brine, dried over anhydrous sodium sulfate and evaporated. The residue was crystallized from toluene to give the above named product as white prisms, m.p. 142°–147°.

EXAMPLE 27

Preparation of
5-Chloro-2-fluoro-2-(2-hydroxyethyl)aminobenzophenone

A solution of 10g (0.04 M) of 2-amino-5-chloro-2'-flurobenzophenone in 100 ml of dry benzene was treated with 10.6g (0.08 M) of aluminium chloride under nitrogen. The reaction mixture was next treated with 7g (0.16 M) of ethylene oxide (5 minute period), keeping the temperature below 35° with an ice bath. After 65 hours at room temperature, the procedure was repeated using the same amounts of aluminium chloride and ethylene oxide as before. After 5 hours at room temperature, the benzene was removed by distillation, and the residue was made basic with ammonium hydroxide, stirred with 100 ml of dichloromethane and filtered. The organic layer was separated, washed with saturated brine, dried over anhydrous sodium sulfate and evaporated to dryness. The product was recrystalized three times from a mixture of ether and petroleum ether to give the above named product as yellow needles, m.p. 96°–101°.

EXAMPLE 28

Preparation of
2-(2-Acetoxyethylamino)-5-chloro-2'-fluorobenzophenone

A solution of 15g (0.0516 M) of 5-chloro-2-fluoro-2-(2-hydroxyethyl)amino-benzophenone in 75 ml of acetic anhydride was heated on the steam bath for 1 hour. Solvent was removed under reduced pressure and the residue was dissolved in 75 ml of benzene. This solution was filtered through a column of 100g of silica gel. The column was eluted with 500ml of benzene which was discarded, and 1 l. of dichloromethane. Removal of the dichloromethane gave a residue which was crystallized from a mixture of ether and petroleum ether to give the above named product as yellow rods, m.p. 48°–55°.

EXAMPLE 29

Preparation of
2-[N-(2-Acetoxyethy)-N-(2-bromacetyl)amino]-5-chloro-2'-fluorobenzophenone A mixture of 2.5g (0.0074 M) of 2-(2-acetoxyethylamino)-5-chloro-2'-flurobenzophenone and 5g (0.0362 M) of potassium carbonate in 25 ml of dry chloroform was treated with 2.0g (0.0096 M) of bromoacetyl bromide over a 20 minute period with stirring. The mixture was stirred for 1 hour at room temperature when 25 ml of water was added, and the chloroform layer was separated. The organic layer was washed with saturated brine, dried over anhydrous sodium sulfate and evaporated to dryness. The residual oil was dissolved in 10 ml of benzene, and chromatographed over 100g of Florisil. Elution with 1 l. of benzene gave 0.2g of an oil and elution with 1.5 l. of ether and 1 l. of ethyl acetate gave 1.8g and 1.0g, respectively of a colorless oil which were combined and recrystallized from a mixture of dichloromethane and petroluem ether to give the above named product as white prisms, m.p. 84°–88°.

EXAMPLE 30

Preparation of 7-(2-Acetoxyethyl)-10-chloro-11b-(2-fluorophenyl)-2,3,5,11b-tetrahydrooxazolo[3,2-d][1,4]benzodiazepin-6(7H)-one A solution containing 1.5g (0.0033 M) of 2-[N-(2-acetoxyethyl)-N-(2-bromoacetyl)amino]-5-chloro-2'-fluorobenzophenone, 0.5 ml of triethylamine and 0.23g (0.0036 M) of ethanolamine in 15 ml of benzene was kept at room temperature for 65 hours and then was partitioned between 25 ml of ethyl acetate and 25 ml of water. The organic layer was separated, washed with saturated brine, dried over anhydrous sodium sulfate and evaporated to dryness. The residue was partioned between 20 ml of ether and 20 ml of 1N hydrochloric acid. The acid layer was separated and extracted with 25 ml of ethyl acetate. The organic layer was then washed with 20 ml of dilute ammonium hydroxide, dried over anhydrous sodium sulfate and evaporated to dryness. The residual oil was crystallized from ether and recrystallized from a mixture of methanol and water to give the above named product as white prisms, m.p. 120°–123°.

EXAMPLE 31

Preparation of 10-Chloro-11b-(2-fluorophenyl)-7-(2-hydroxyethyl)-2,3,5,11b-tetrahydrooxazolo(3,2-d)[1,4]benzodiazepin-6-(7H)-one A solution of 0.5g (0.0012 M) of 7-(2-acetoxyethyl)-10-chloro-11b-(2-fluorophenyl)-2,3,5,11b-tetrahydrooxazolo[3,2-d] [1,4]benzodiazepin-6(7H)-one in 5 ml of methanol was treated with 2 ml of 3N sodium hydroxide. After 3 hours, 50 ml of water was added and the solution was extracted with 40 ml of dichloromethane, which was then dried over anhydrous sodium sulfate and evaporated to dryness. The residue was crystallized from a mixture of methanol and water to give 10-chloro-11b-(2-fluorophenyl)-7-(2-hydroxyethyl)-2,3,5,11b-tetrahydrooxazolo)3,2-d) [1,4]benzodiazepin-6(7H)-one as white prisms, m.p. and m.m.p. 141°–146°.

EXAMPLE 32

The pharmacological activity of a series of compounds of the present invention was determined in standard screening tests. Compounds which were employed in these experiments were as follows:

10-chloro-7-(2-hydroxyethyl)-2,3,5,11b-tetrahydro-11b-phenyloxazolo[3,2-d][1,4]benzodiazepin-6-(7H)-one (COMPOUND A) and
10-chloro-11b-(2-fluorophenyl)-b 7-(2-hydroxyethyl)-2,3,5,11b-tetrahydrooxazolo[3,2-d][1,4]benzodiazepin-6-(7H)-one (COMPOUND B).

The tests employed in this experiment were the following:

Foot Shock

This test is a screen for compounds having muscle relaxant and/or anti-anxiety (tranquilizer) activity. A pair of mice is confined under a 1 liter beaker placed on a grid which presents shock to the feet. At least five fighting episodes are elicited in a 2-minute period. Pairs of mice are marked and pretreated by oral dosage 1 hour prior to a second shocking. Logarithmic-dose intervals are utilized up to a maximum of 100 mg/kgm. At the 100 per cent blocking dose, three out of three pairs must be blocked from fighting.

Inclined Screen

The test is useful in determining muscle relaxant and/or sedative activity. Groups of six male mice are given the test drug (maximum dose of 500 mg/kg.) and then are left on the inclined screen at least four hours for observation of paralyzing effects severe enough to cause them to slide off the screen. If activity is observed, additional doses are tested until at least two are reached at which some, but not all the animals slide off the screen. Doses at which mice fall off the screen due to toxicity or excitation are not included in the calculation of $PD_{50}$. The $PD_{50}$ is determined from a graph on which dose is plotted against per cent of mice paralyzed. This $PD_{50}$ value is defined as the dose in mg/kg. which can be expected to cause 50 per cent of mice to slide off the screen.

Unanesthetized Cat

Cats are treated orally and observed for minimum symptoms—usually ataxia. One cat is used at a dose of 50 mgm/kgm. If activity is present, up to three cats/dose are used. Results are given as minimum effective dose. This test is useful in determining muscle relaxant activity.

Antimetrazol

This test determines anticonvulsant and/or sedative activity of compounds in mice. The test compound is administered orally to groups of four mice at various dose levels. One hour later, metrazol (at a dose level previously determined to be sufficient to induce convulsive seizures in all test animals ~125 mg/kg.) is administered subcutaneously and the animals are observed for protection from convulsive seizures. Results are recorded as the number of animals protected against convulsions. The dose at which 50 per cent of the animals are protected from convulsive seizures is expressed as the $ED_{50}$.

The test results from the above tests using indicated compounds of the present invention are summarized below in Table I.

TABLE I

| Compound | Footshock 100% Blocking Dose Level | Inclined Screen PD$_{50}$ | Unanesthetized Cat MED | Antimetrazole ED$_{50}$ |
| --- | --- | --- | --- | --- |
| Compound A | 20 mg. | 50 mg. | 5 mg. | — |
| Compound B | 4 mg. | 15 mg. | 5 mg. | 2.034 mg. |

EXAMPLE 33

COMPOUND B (10-chloro-11b-(2-fluorophenyl-7-(2-hydroxyethyl)-2,3,,5,11b-tetrahydrooxazolo[3,2-d][1,4]benzodiazepin-6-(7H)-one) was prepared in the form of several pharmacological formulations as follows:

A. Suppository Formulation

| | Per 1.3 Gm. Suppository |
| --- | --- |
| 10-Chloro-11b-(2-fluorophenyl)-7-(2-hydroxyethyl)-2,3,5,11b-tetrahydrooxazolo[3,2-d][1,4]benzodiazepin-6-(7H)-one | 0.010 Gm. |
| Wecobee M* | 1.245 Gm. |
| Carnauba Wax | 0.045 Gm. |

*E. F. Drew Company
522 Fifth Ave
New York, New York

Procedure:

1. The Wecobee M and the carnauba wax were melted in a suitable size glass-lined container (stainless steel may also be used), mixed well and cooled to 45°C. The 10-Chloro-11b-(2-fluorophenyl)-7-(2-hydroxyethyl)-2,3,5,11b-tetrahydrooxazolo[3,2-d][1,4]benzodiazepin-6-(7H)-one which had been reduced to a fine powder with no lumps, was added and stirred until completely and uniformly dispersed.

2.

3. The mixture was poured into suppository molds to yield suppositories having an individual weight of 1.3 Grams.

4. The suppositories were cooled and removed from molds. They were then individually wrapped in wax paper for packaging (foil may also be used).

B. Capsule Formulation

| | Per Capsule |
| --- | --- |
| 10-Chloro-11b-(2-fluorophenyl)-7-(2-hydroxyethyl)-2,3,5,11b-tetrahydrooxazolo[3,2-d][1,4]benzodiazepin-6-(7H)-one | 10 Mg. |
| Lactose, U.S.P. | 165 Mg. |
| Corn Starch, U.S.P. | 30 Mg. |
| Talc, U.S.P. | 5 Mg. |
| Total Weight | 210 Mg. |

Procedure 1. 10-Chloro-11b-(2-fluorophenyl)-7-(2-hydroxyethyl)-2,3,5,11b-tetrahydrooxazolo[3,2-d][1,4]benzodiazepin-6-(7H)-one, lactose and corn starch were mixed in a suitable mixer.

2. The mixture was further blended by passing through a Fitzpatrick Comminuting Machine with a No. 1A screen with knives forward.

3. The blended powder was returned to the mixer, the talc added and blended thoroughly.

4. The mixture was filled into No. 4 hard shell gelatin capsules on a Parke Davis capsulating machine. (Any similar type capsulating machine may be used.)

C. Parenteral Formulation

| | Per cc |
| --- | --- |
| 10-Chloro-11b-(2-fluorophenyl)-7-(2-hydroxyethyl)-2,3,5,11b-tetrahydrooxazolo[3,2-d][1,4]benzodiazepin-6-(7H)-one | 5.0 Mg. |
| Propylene Glycol | 0.4 CC. |
| Benzyl Alcohol (Benzaldehyde free) | 0.015 CC. |
| Ethanol 95 percent U.S.P. | 0.10 CC. |
| Sodium Benzoate | 48.8 Mg. |
| Benzoic Acid | 1.2 Mg. |
| Water for Injection q.s. | 1.0 CC. |

Procedure (For 10,000 cc)

1. The 50 Grams of 10-chloro-11b-(2-fluorophenyl)-7-(2-hydroxyethyl)-2,3,5,11b-tetrahydrooxazolo[3,2-d][1,4]-benzodiazepin-6-(7H)-one were dissolved in 150 cc of benzyl alcohol; 4,000 cc of propylene glycol and 1,000 cc of ethanol were added.

2. The 12 Grams of benzoic acid were dissolved in the above. The 48.8 Grams of sodium benzoate dissolved in 3,000 cc of Water for Injection were added. The solution was brought up to final volume of 10,000 cc with Water for Injection.

3. The solution was filtered through an 02 Selas candle, filled into suitable size ampuls, gassed with N$_2$ and sealed. It was then autoclaved at 10 psi for 30 minutes.

D. Tablet Formulation

| | Per Tablet |
| --- | --- |
| 10-Chloro-11b-(2-fluorophenyl)-7-(2-hydroxyethyl)-2,3,5,11b-tetrahydrooxazolo[3,2-d][1,4]benzodiazepin-6-(7H)-one | 25.00 Mg. |
| Dicalcium Phosphate Dihydrate, Unmilled | 175.00 Mg. |
| Corn Starch | 24.00 Mg. |
| Magnesium Stearate | 1.00 Mg. |
| Total Weight | 225.00 Mg. |

Procedure 1. 10-Chloro-11b-(2-fluorophenyl)-7-(2-hydroxyethyl)-2,3,5,11b-tetrahydrooxazolo[3,2-d][1,4]-benzodiazepin-6-(7H)-one and corn starch were mixed together and passed through an No. 00 screen in Model J Fitzmill with hammers forward.

2. This permix was then mixed with dicalcium phosphate and one-half of the magnesium stearate, passed through a No. 1A screen in Model J Fitzmill with knives forward, and slugged.

3. The slugs were passed through a No. 2A plate in a Model D Fitzmill at slow speed with knives forward, and the remaining magnesium stearate was added.

4. The mixture was mixed and compressed.

We claim:

1. A compound of the formula

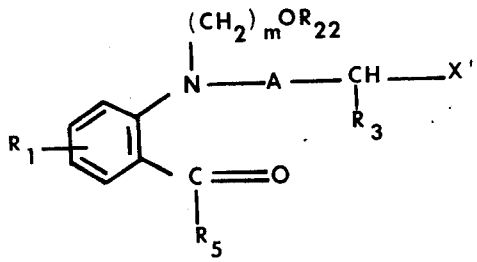

wherein $R_1$ is hydrogen, nitro, trifluoromethyl, halogen, lower alkyl, lower alkyl mercapto or lower alkoxy; $R_3$ is hydrogen or lower alkyl; $R_5$ is phenyl or phenyl substituted with a member selected from the group consisting of halogen, nitro, trifluoromethyl and lower alkyl; $R_{22}$ is an acyl moiety derived from a lower alkanoic acid; m is an integer from 1-7; A is selected from the group consisting of $-CH_2-$ and

and X' is chlorine, bromine or iodine.

2. A compound of claim 1 wherein the acyl group is acetyl.

3. The compounds of claim 1 wherein $R_1$ is halogen and is joined to the 5-position of the ketone, A is C=O, and $R_5$ is selected from the group consisting of phenyl and o-halophenyl.

4. The compounds of claim 3 wherein $R_1$ is chlorine, $R_3$ is hydrogen, $R_5$ is o-fluorophenyl, $R_{22}$ is acetyl, m is 2 and X' is bromine, i.e. a compound of the formula 2-[N-(2-acetoxyethyl)-N-(2-bromoacetyl)amino]-5-chloro-2'-fluorobenzophenone.

* * * * *